(12) United States Patent
Kim et al.

(10) Patent No.: US 11,591,427 B2
(45) Date of Patent: Feb. 28, 2023

(54) DENTAL COMPOSITE COMPRISING GLASS CERAMIC

(71) Applicant: HASS CO., LTD., Gangneung-si (KR)

(72) Inventors: Yong Su Kim, Gangneung-si (KR); Hyung Bong Lim, Ansan-si (KR); Kyung Sik Oh, Incheon (KR); Sung Min Kim, Yongin-si (KR); Young Pyo Hong, Gangneung-si (KR); Joon Hyung Kim, Anseong-si (KR); Si Won Son, Seoul (KR); Yena Kim, Seoul (KR)

(73) Assignee: HASS CO., LTD., Gangneung-si (KR)

(*) Notice: Subject to any disclaimer, the term of this patent is extended or adjusted under 35 U.S.C. 154(b) by 398 days.

(21) Appl. No.: 16/954,779

(22) PCT Filed: Feb. 4, 2020

(86) PCT No.: PCT/KR2020/001619
§ 371 (c)(1),
(2) Date: Jun. 17, 2020

(87) PCT Pub. No.: WO2020/166869
PCT Pub. Date: Aug. 20, 2020

(65) Prior Publication Data
US 2021/0214483 A1   Jul. 15, 2021

(30) Foreign Application Priority Data

Feb. 12, 2019   (KR) ........................ 10-2019-0016380

(51) Int. Cl.
| | | |
|---|---|---|
| *C08F 222/10* | (2006.01) | |
| *C03C 10/00* | (2006.01) | |
| *C08F 222/22* | (2006.01) | |
| *C08K 9/06* | (2006.01) | |
| *C08K 3/40* | (2006.01) | |
| *A61K 6/833* | (2020.01) | |
| *A61K 6/60* | (2020.01) | |
| *C03C 17/30* | (2006.01) | |

(52) U.S. Cl.
CPC .......... *C08F 222/1063* (2020.02); *A61K 6/60* (2020.01); *A61K 6/833* (2020.01); *C03C 10/0009* (2013.01); *C03C 17/30* (2013.01); *C08F 222/22* (2013.01); *C08K 3/40* (2013.01); *C08K 9/06* (2013.01); *C03C 2204/00* (2013.01)

(58) Field of Classification Search
None
See application file for complete search history.

(56) References Cited

U.S. PATENT DOCUMENTS

| | | | | |
|---|---|---|---|---|
| 5,804,520 A | * | 9/1998 | Morinaga | ............... C03C 10/00 501/4 |
| 6,455,451 B1 | * | 9/2002 | Brodkin | ................. A61K 6/818 264/16 |
| 7,846,857 B2 | * | 12/2010 | Holand | ..................... A61K 6/78 106/35 |
| 7,927,538 B2 | | 4/2011 | Moszner et al. | |
| 9,757,311 B2 | * | 9/2017 | Rampf | .................. C03C 4/0021 |
| 10,315,289 B2 | * | 6/2019 | Kasai | ....................... B24D 3/14 |
| 2014/0336304 A1 | | 11/2014 | Ruppert et al. | |
| 2018/0257973 A1 | | 9/2018 | Kim et al. | |

FOREIGN PATENT DOCUMENTS

| | | |
|---|---|---|
| JP | 2018-145084 A | 9/2018 |
| KR | 10-1325281 B1 | 11/2013 |
| KR | 10-2014-0132694 A | 11/2014 |
| KR | 10-2018-0102711 A | 9/2018 |
| WO | 2012/161363 A1 | 11/2012 |

OTHER PUBLICATIONS

Park, Jin-Hong et al. "Fabrication of Composite Resin Block Using Lithium Disilicate Glass-Ceramics for Dental CAD/CAM Restoration". Korean Journal of Society for Dental Materials, 2016, vol. 43, No. 3, pp. 247-256.

* cited by examiner

*Primary Examiner* — Tae H Yoon
(74) *Attorney, Agent, or Firm* — Novick, Kim & Lee PLLC; Jae Youn Kim

(57) ABSTRACT

Dental composite composition including a glass ceramic and a curable organic material is described in which the glass ceramic includes a crystal phase having an average grain size of 50 to 400 nm, and the dental composite composition is provided as a dental prosthetic material exhibiting superior transparency and mechanical properties comparing to conventional composite products containing micro-sized crystal grains and also has excellent aesthetics and processability required for prosthetic materials for same-day dental prosthetic service.

8 Claims, 2 Drawing Sheets

DENTAL COMPOSITE COMPRISING GLASS CERAMIC

TECHNICAL FIELD

The present invention relates to a dental composite comprising glass ceramic, and more particularly to a dental composite imparted with improved translucency and mechanical properties by hybridizing organic and inorganic materials by controlling the crystal size of glass ceramic used in dental prostheses.

BACKGROUND ART

Porcelain and metal, which are conventionally used prosthetic materials, are, with the development of the dental industry, becoming problematic in terms of physical properties or tooth aesthetics, and the market share thereof is gradually decreasing. Meanwhile, the market share of replacement materials such as glass ceramic, zirconia and the like is increasing. Moreover, a hot-pressing process, which is conventionally used to manufacture prostheses, takes a long period of time to manufacture prostheses, so it is difficult to manufacture a prosthesis in one day, as required in the current dental market, thus triggering a change to CAD/CAM systems. In order to support this change, the effectiveness of materials for 1:1 processing capable of implantation immediately after processing without additional heat treatment, as is the case with glass ceramic, is also improving.

Due to the development of zirconia, glass ceramic and the like, materials showing good aesthetics and desirable physical properties are mainly used. However, most ceramic materials undergo crystallization heat treatment after processing, making it difficult to use the same to provide same-day prosthetic service.

Furthermore, a ceramic material that is currently subjected to 1:1 processing is problematic because the processability thereof is low due to the use of a ceramic material, which has already been subjected to crystallization, and because fracture occurs in the margin portion (the boundary between the prosthesis and the tooth).

With the goal of solving these problems and fulfilling the requirements of the current dental market, a composite in which organic and inorganic materials are hybridized has been developed. The composite is a complementary material in which the organic material serves to reduce brittleness, which is the disadvantage with the inorganic material, and the inorganic material serves to improve the physical properties of the organic material, such as the low strength thereof. Moreover, since the composite may be advantageously used for 1:1 processing capable of implantation in the oral cavity immediately after processing, new products thereof are being introduced through continuous technical development. The composite has strength of about 150 to 200 MPa depending on the type of currently commercialized product, and the processability thereof is also superior to that of conventional glass-ceramics capable of being used for 1:1 processing.

With regard to the manufacture of such a composite, Korean Patent No. 10-1325281 discloses a dental composite composition comprising a glass ceramic-ceramic, a monomer and/or oligomer having an unsaturated double bond, a polymerization initiator for initiating polymerization, and a nano-sized filler. Here, it is disclosed that a composite composition having superior mechanical strength, aesthetics and abrasion resistance may be obtained by adding barium aluminosilicate as the inorganic filler and adjusting the amount of glass ceramic-ceramic.

Moreover, Korean Patent Application Publication No. 10-2014-0132694 discloses a dental material including (a) at least one curable monomer and/or polymer and (b) at least one filler, in which the (b) at least one filler includes agglomerated oxide particles, the oxide particles include a matrix and a doping component, the matrix includes silicon dioxide, and the doping component includes zirconium dioxide. Here, it is disclosed that the transparency of the dental material may be improved using, as the filler, agglomerated silicon dioxide primary particles doped with zirconium dioxide.

In addition, there are a number of conventional documents related to methods of manufacturing a composite, which is a prosthetic material for teeth, but as the use of the composite as a dental prosthesis material increases, new technologies are continuously being added through research and development of superior products.

DISCLOSURE

Technical Problem

An objective of the present invention is to provide a dental composite that may facilitate 1:1 processing and may exhibit superior translucency and mechanical properties when used as a prosthetic material for same-day service.

Technical Solution

In order to accomplish the above objective, the present invention provides a dental composite composition comprising a glass ceramic and a curable organic material, in which the glass ceramic comprises a crystal phase having an average grain size of 50 to 400 nm.

In the dental composite according to a preferred embodiment of the present invention, the glass ceramic may be controlled in the size of the crystal phase through crystallization heat treatment at 500 to 800° C.

In the dental composite according to an embodiment of the present invention, the glass ceramic may be lithium disilicate glass ceramic.

In the dental composite according to a preferred embodiment, the glass ceramic may be surface-treated with organofunctional silane.

In the dental composite according to a preferred embodiment, in consideration of chemical bonding, the organofunctional silane may be a silane-coupling agent having a (meth)acryl group, and a specific example of the organofunctional silane may be at least one selected from the group consisting of methacryloxyalkylene trialkoxysilane, 3-methacryloxypropyl trimethoxysilane and 3-methacryloxypropyl triethoxysilane.

In the dental composite according to a preferred embodiment of the present invention, the curable organic material may be selected from among (meth)acrylate monomers and oligomers having unsaturated double bonds.

In the dental composite according to a preferred embodiment of the present invention, the curable organic material may be at least one selected from the group consisting of hydroxyethyl methacrylate (HEMA), 2,2-bis[4-(2-hydroxy-3-methacryloyloxypropoxy)phenyl] propane (Bis-GMA), triethylene glycol dimethacrylate (TEGDMA), diurethane dimethacrylate (UDMA), urethane dimethacrylate (UDM), biphenyl dimethacrylate (BPDM), n-tolylglycine glycidyl methacrylate (NTGE), polyethylene glycol dimethacrylate (PEG-DMA) and oligocarbonate dimethacrylic esters.

Advantageous Effects

According to the present invention, an organic/inorganic hybrid composite can be provided as a dental prosthetic material, which comprised a glass ceramic containing nano-sized crystal grains and thus can exhibit high transparency and superior mechanical properties compared to conventional composite products containing micro-sized crystal grains and also has excellent aesthetics and processability, required for prosthetic materials for same-day dental prosthetic service.

BEST MODE

The above and additional aspects of the present invention will become more apparent through preferred embodiments described with reference to the accompanying drawings. Hereinafter, a detailed description will be given of embodiments of the present invention so that those skilled in the art may easily understand and reproduce the same.

The present inventors have ascertained that the translucency and mechanical properties of a composite may be improved by controlling the crystal size of glass ceramic, which is an inorganic material of the composite, and also that when light is transmitted through glass ceramic containing nano-sized crystals in the dental composite composition of the present invention, not only translucency but also mechanical properties may be improved compared to when using large crystal grains (micro-size or larger), thus culminating in the present invention.

Specifically, the present invention pertains to a dental composite composition comprising a glass ceramic and a curable organic material, in which the glass ceramic comprises a crystal phase having an average grain size of 50 to 400 nm.

The glass-ceramics is imparted with the physical properties of both crystalline ceramics and glass by heat-treating starting glass, and is used as a dental prosthetic material taking into consideration biocompatibility, semitransparency, and mechanical properties. The prosthetic material is mainly $SiO_2$—$Al_2O_3$—$K_2O$-based leucite glass ceramic or $SiO_2$—$Li_2O$-based lithium disilicate glass ceramic.

This glass ceramic is manufactured by preparing a glass precursor and performing crystallization heat treatment. Here, as the temperature at which the amorphous glass precursor is subjected to crystallization heat treatment increases, the average grain size of crystal phases increases, the crystal length becomes longer, and the amount of crystals increases.

However, in the present invention, the average grain size of crystal phases is controlled in the range of 50 to 400 nm, whereby a composite including the same is improved in both transparency and mechanical properties.

The composite according to the present invention is very suitable for use in same-day CAD/CAM dental prosthetic service because it exhibits color, physical properties and processability very similar to those of teeth.

In order for the composite to exhibit color and physical properties similar to those of teeth, various variables, such as the ratio of inorganic and organic materials, the crystal size of the inorganic material, the grain size and distribution of the inorganic material, the use of a silane-coupling agent, and the type of initiator, have to be met. To this end, the present invention provides the most suitable method in order to reproduce an appearance similar to that of natural teeth.

Figure 1:
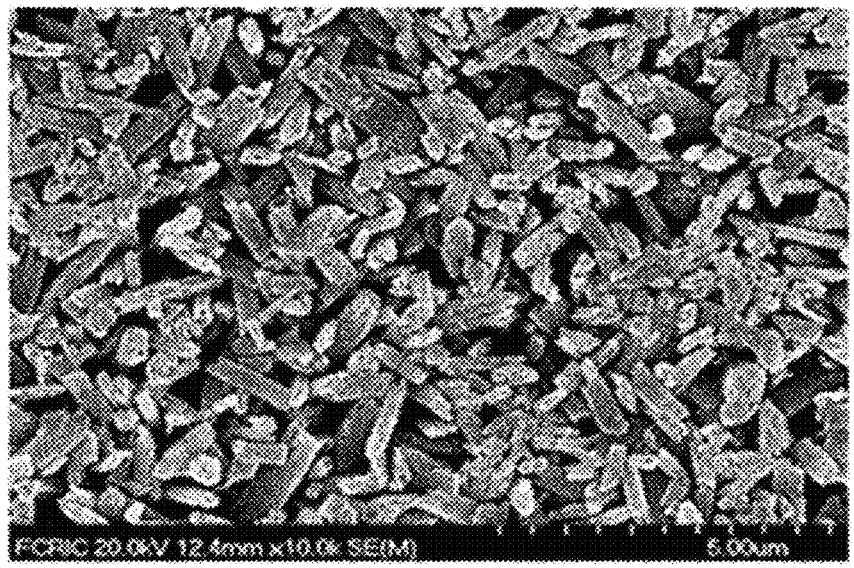
FIG. 1 is a scanning electron microscope (SEM) image showing the glass ceramic containing micro-sized crystal phase.

Typically, glass ceramic obtained by performing crystallization heat treatment at a high temperature of 1,000° C. or more is used in the manufacture of dental composites. In this case, micro-sized crystals having a size of about 2 to 5 μm are formed as shown in FIG. 1. When a composite containing such crystals is manufactured, it has undesirable transparency.

Therefore, the present inventors have endeavored to improve the transparency of a dental composite including glass ceramic and thus have ascertained that when the crystals of glass ceramic have an average grain size of 50 to 400 nm, the transparency thereof is remarkably improved compared to glass ceramic containing micro-sized crystals. Moreover, it is confirmed that despite the decreased crystal size, mechanical properties such as biaxial flexural strength and Vickers hardness are improved. When the crystal size of the glass ceramic is larger than the above range, it affects light reflection and the like and thus opaque properties appear.

As for the glass ceramic having a crystal size falling in the above range, the crystal size thereof may be controlled in the above range by performing crystallization heat treatment in the range of from 500 to 800° C. When lithium disilicate glass ceramic or leucite glass ceramic is subjected to crystallization heat treatment in the above temperature range, glass ceramic containing crystals having an average grain size of 50 to 400 nm may be obtained.

Meanwhile, in the manufacture of a dental composite according to the present invention, the surface of the glass ceramic containing nano-sized crystals falling in the above crystal size range may be treated with organofunctional silane. The treatment of the surface of glass ceramic with organofunctional silane may also serve in order for the composite to exhibit a color and physical properties similar to those of teeth depending on the form of coupling of the inorganic glass ceramic and the organic material in the dental composite. When the surface of glass ceramic is treated with organofunctional silane and then reacted with a curable organic material, chemical bonding between the glass ceramic and the organofunctional silane and also chemical bonding between the organofunctional silane and the curable organic material may be induced.

Moreover, in the curable organic material, shrinkage hardening occurs during the polymerization reaction, and thus, the use of organofunctional silane is effective at minimizing a change in physical properties owing to shrinkage hardening.

In the composite according to a preferred embodiment, in consideration of such chemical bonding, the organofunctional silane may be a silane-coupling agent having a (meth)acryl group, and more specifically, the organofunctional silane may be at least one selected from the group consisting of methacryloxyalkylene trialkoxysilane, 3-methacryloxypropyl trimethoxysilane and 3-methacryloxypropyl triethoxysilane, but is not limited thereto.

The surface treatment of glass ceramic using organofunctional silane may be performed using a solution of organofunctional silane diluted in ethanol in consideration of the specificity of a dental composite.

When the surface of the glass ceramic is treated with organofunctional silane to afford a composite, the vol % of the inorganic material based on the total volume of the composite may increase, making it possible to increase biaxial flexural strength and hardness.

In the dental composite of the present invention, the curable organic material may include a polymerizable monomer and/or oligomer, which are typically useful in dental composites. For example, the curable organic material may be selected from among (meth)acrylate monomers and oligomers having unsaturated double bonds.

A specific example of the curable organic material may be at least one selected from the group consisting of hydroxyethyl methacrylate (HEMA), 2,2-bis[4-(2-hydroxy-3-methacryloyloxypropoxy)phenyl]propane (Bis-GMA), triethylene glycol dimethacrylate (TEGDMA), diurethane dimethacrylate (UDMA), urethane dimethacrylate (UDM), biphenyl dimethacrylate (BPDM), n-tolylglycine glycidyl methacrylate (NTGE), polyethylene glycol dimethacrylate (PEG-DMA) and oligocarbonate dimethacrylic esters. Among examples of the monomers and/or oligomers, UDMA or Bis-GMA has high viscosity, making it difficult to infiltrate a porous inorganic material therewith, and therefore, may be mixed with TEGDMA having low viscosity at a mass ratio of 5:5 to 6:4, but the present invention is not limited thereto.

Meanwhile, the composite may include an initiator in order to crosslink the curable organic material into a polymer and cure the same, and examples of the initiator include a photoinitiator and a thermal initiator. In the present invention, a thermal initiator is preferably used, and it is possible to obtain a composite having superior physical properties when performing thermal polymerization using a thermal initiator compared to when performing photopolymerization using a photoinitiator.

The thermal initiator may include various compounds known in the art, and examples thereof may include, but are not limited to, known peroxides such as dibenzoyl peroxide, dilauroyl peroxide, tert-butyl peroctoate, tert-butyl perbenzoate, etc.

As described above, in order for the composite to exhibit a color and physical properties similar to those of teeth, various variables, such as the ratio of inorganic and organic materials, the crystal size of the inorganic material, the grain size and distribution of the inorganic material, the use of the silane-coupling agent, and the type of initiator, need to be controlled. Accordingly, in the composite composition of the present invention, the amount of the glass ceramic is preferably 70 to 85 wt % based on a total of 100 wt % of the composite composition, and the amount of the curable organic material is preferably 15 to 30 wt % based on a total of 100 wt % of the composite composition.

The amount of the polymerization initiator may be adjusted in consideration of the amount of the curable organic material, and is preferably about 1 to 5 parts by weight based on 100 parts by weight of the curable organic material.

The composite thus manufactured may be configured such that the volume of the inorganic component is 60 to 80 vol % based on the total volume of the composite and such that the volume of the organic component is 20 to 40 vol % based on the total volume of the composite. As for the vol % of the inorganic and organic materials of the composite, the volume fraction of the inorganic material may be substantially increased due to treatment with organofunctional silane.

The dental composite according to the present invention may be a filling composite, a veneer composite, a green compact of an artificial tooth, a green compact of a veneer, a green compact of an inlay, a green compact of an implant, or a green compact of a cutting block for the manufacture of dental prostheses according to a CAD/CAM technique or the manufacture of the aforementioned dental materials.

MODE FOR INVENTION

A better understanding of the present invention will be given through the following examples. These examples are merely set forth to illustrate the present invention, and are not to be construed as limiting the scope of the present invention.

Figure 2:
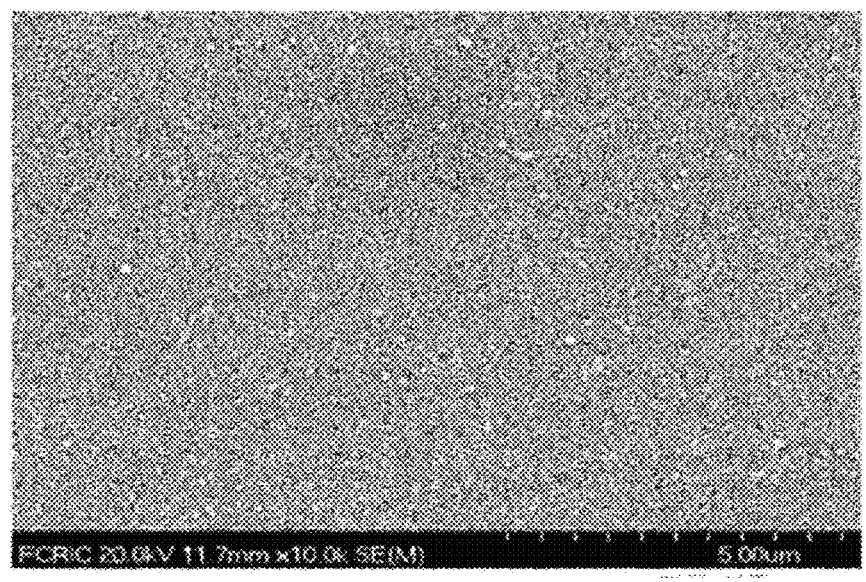
FIG. 2 is an SEM image showing the glass ceramic containing nano-sized crystal phase.

The crystal size of the lithium disilicate glass ceramic used in Comparative Example 1 and Example 1 was measured using a scanning electron microscope (SEM, JSM-7610F FE-SEM, made by JEOL). The results thereof are shown in FIGS. 1 and 2. When the surface thereof was observed with SEM, the crystallized sample was etched with an acid, and the surface thereof was observed.

As shown in FIGS. 1 and 2, the glass ceramic used in Example 1 manifested nano-sized crystal grains, and the glass ceramic used in Comparative Example 1 manifested micro-sized crystal grains.

Specifically, the crystal size of the glass ceramic used in Comparative Example 1 was analyzed to have an average grain size of 2 to 5 µm, and the crystal size of the glass ceramic used in Example 1 was analyzed to have an average grain size of 50 to 400 nm.

Comparative Example 1: Manufacture of Composite from Glass Ceramic Having Micro-Crystal Size As shown in FIG. 1, a composite was manufactured using lithium disilicate glass ceramic having a micro-crystal size, obtained by performing crystallization heat treatment at 1,000 to 1,200° C.

The composite was manufactured through silane treatment, mixing of inorganic and organic materials, and curing. For silane treatment, 3-methacryloxypropyl triethoxysilane was mixed in an amount of 5 to 15 vol % with ethanol, adjusted to a pH of 4.2 to 5.0 using acetic acid, added with the prepared inorganic material, and then maintained for at least 12 hr, after which the silane-treated inorganic material was dried in an oven at 100° C. The inorganic material was lithium disilicate glass ceramic, as mentioned above, and the organic material was used by mixing triethylene glycol dimethacrylate (TEGDMA) and diurethane dimethacrylate (UDMA) at 4:6 to 5:5. The dried inorganic material was sufficiently mixed with the organic material at a mass ratio of 7:4 or 8:2 and then cured at 100° C., thereby manufacturing a dental composite.

Example 1: Manufacture of Composite from Glass Ceramic Having Nano-Crystal Size As shown in FIG. 2, a composite was manufactured using lithium disilicate glass ceramic having a nano-crystal size, obtained by performing crystallization heat treatment at 500 to 800° C.

The composite was manufactured through silane treatment, mixing of inorganic and organic materials, and curing. For silane treatment, 3-methacryloxypropyl triethoxysilane was mixed in an amount of 5 to 15 vol % with ethanol, adjusted to a pH of 4.2 to 5.0 using acetic acid, added with the prepared inorganic material, and then maintained for at least 12 hr, after which the silane-treated inorganic material was dried in an oven at 100° C. The inorganic material was lithium disilicate glass ceramic, as mentioned above, and the organic material was used by mixing triethylene glycol dimethacrylate (TEGDMA) and diurethane dimethacrylate (UDMA) at 4:6 to 5:5. The dried inorganic material was sufficiently mixed with the organic material at a mass ratio of 7:4 or 8:2 and then cured at 100° C., thereby manufacturing a dental composite.

Test Example

The light transmittance of the composites obtained in Example 1 and Comparative Example 1 was measured. The results thereof are shown in Table 1 below.

The light transmittance was measured using a UV spectrophotometer (V570, made by Jasco), the sample was manufactured to a thickness of 1.2 mm, and the average light transmittance thereof was determined in the visible light range (380 to 780 nm).

TABLE 1

| No. | Light transmittance (%) |
|---|---|
| Example 1 | 30-60 |
| Comparative Example 1 | 18-25 |

As is apparent from Table 1, when the crystals were nano-sized, translucency was improved compared to the conventional case.

Meanwhile, in order to evaluate the effect of the crystal size of glass ceramic on mechanical properties, biaxial flexural strength and Vickers hardness were measured.

Here, biaxial flexural strength was measured in accordance with ISO 6872: 2015, and Vickers hardness was measured as set forth in Journal of Biomedical Optics, Volume 9, Pages 601-608.

Figure 3:
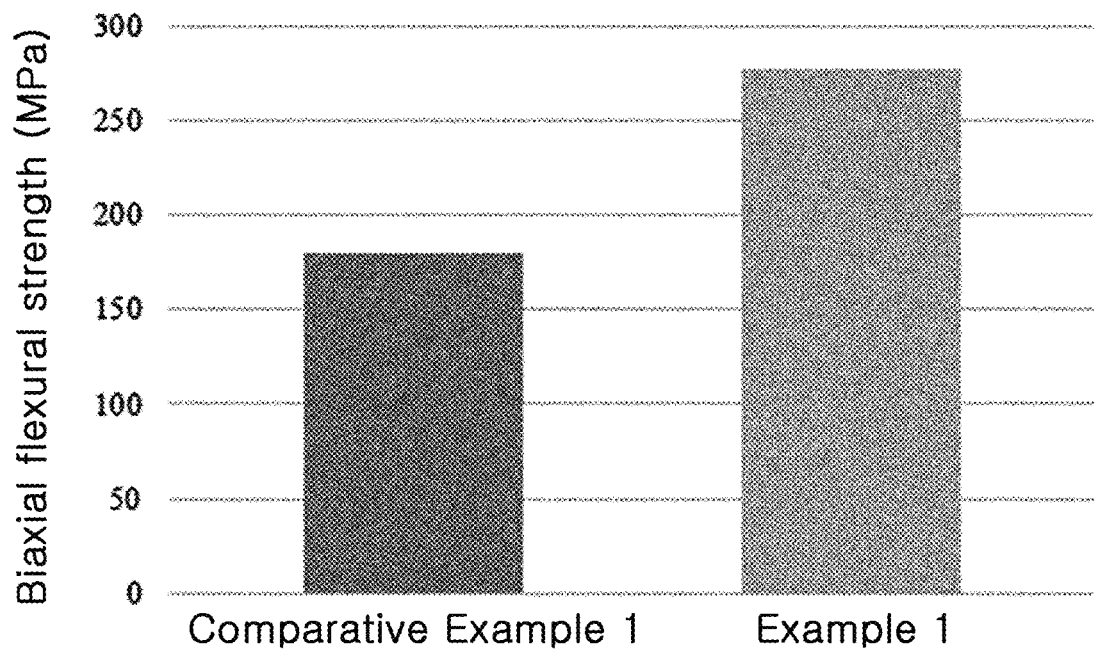
FIG. 3 is a graph showing the results of measurement of biaxial flexural strength of the composite of Comparative Example 1 using micro-sized glass ceramic and the composite of Example 1 using glass ceramic containing nano-sized crystals.
Figure 4:
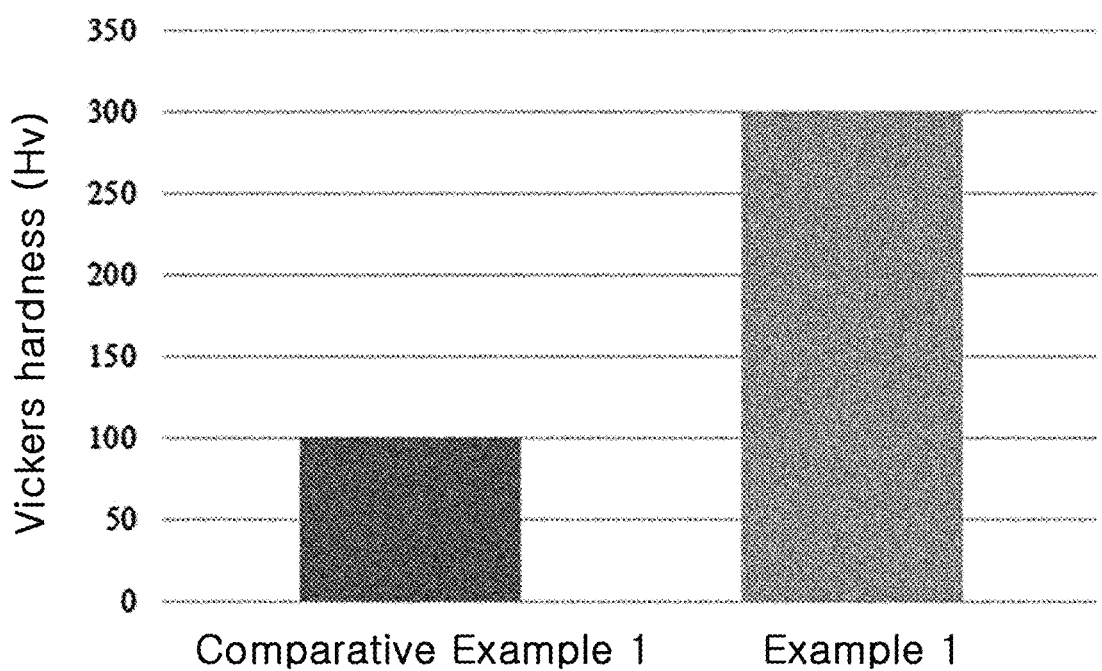
FIG. 4 is a graph showing the results of measurement of Vickers hardness of the composite of Comparative Example 1 using micro-sized glass ceramic and the composite of Example 1 using glass ceramic containing nano-sized crystals.

The results thereof are shown in FIGS. 3 and 4.

FIG. 3 shows the results of measurement of biaxial flexural strength. Here, biaxial flexural strength was increased with a decrease in the crystal size to the nano-scale, and was poor in a conventional micro-sized product. The biaxial flexural strength was about 200 to 300 MPa in the composite manufactured using the nano-sized crystals and was about 150 to 200 MPa when using conventional micro-sized crystals.

FIG. 4 shows the results of measurement of Vickers hardness. The Vickers hardness was about 270 to 300 Hv in the composite manufactured using the nano-sized crystals, and was relatively low, to the level of about 80 to 110 Hv, when using the conventional micro-sized crystals.

When the crystal size of the glass ceramic was at the nano-scale, the physical properties thereof were improved compared to those of conventional products.

Therefore, the present invention is directed to a method of manufacturing a composite having superior physical properties compared to existing products by controlling the crystal size of glass ceramic.

The present invention has been described with reference to an embodiment shown in the drawings, which is merely illustrative, and it will be apparent to those skilled in the art that various modifications and other equivalent embodiments are possible.

INDUSTRIAL APPLICABILITY

The present invention provides a dental composite that facilitates 1:1 processing and exhibits superior translucency and mechanical properties when used as a prosthetic material for same-day service.

The invention claimed is:

1. A dental composite obtained from curing of a composition comprising a glass ceramic and a curable organic material,
    wherein the glass ceramic comprises a crystal phase having an average grain size of 50 to 400 nm, and the dental composite has a biaxial flexural strength of 200 to 300 MPa, and
    a Vickers hardness of 270 to 300 Hv.

2. The dental composite of claim 1, wherein the glass ceramic is controlled in the size of the crystal phase through crystallization heat treatment in the range of from 500 to 800° C.

3. The dental composite of claim 1, wherein the glass ceramic is lithium disilicate glass ceramic.

4. The dental composite of claim 3, wherein the glass ceramic is surface-treated with organofunctional silane.

5. The dental composite of claim 4, wherein the organofunctional silane is a silane-coupling agent having a (meth)acryl group.

6. The dental composite of claim 5, wherein the organofunctional silane is at least one selected from the group consisting of methacryloxyalkylene trialkoxysilane, 3-methacryloxypropyl trimethoxysilane and 3-methacryloxypropyl triethoxysilane.

7. The dental composite of claim 1, wherein the curable organic material is selected from among (meth)acrylate monomers and oligomers having unsaturated double bonds.

8. The dental composite of claim 7, wherein the curable organic material is at least one selected from the group consisting of hydroxyethyl methacrylate (HEMA), 2,2-bis[4-(2-hydroxy-3-methacryloyloxypropoxy)phenyl]propane (Bis-GMA), triethylene glycol dimethacrylate (TEGDMA), diurethane dimethacrylate (UDMA), urethane dimethacrylate (UDM), biphenyl dimethacrylate (BPDM), n-tolylglycine glycidyl methacrylate (NTGE), polyethylene glycol dimethacrylate (PEG-DMA) and oligocarbonate dimethacrylic esters.

* * * * *